United States Patent
Brown

[11] 4,015,598
[45] Apr. 5, 1977

[54] ANAESTHESIC SYSTEM

[76] Inventor: Glenn E. Brown, 24040 Summit Road, Los Gatos, Calif. 95030

[22] Filed: Sept. 5, 1975

[21] Appl. No.: 610,682

[52] U.S. Cl. .............................. 128/188; 128/206; 128/146.5; 128/140 N

[51] Int. Cl.² ..................................... A61M 16/00

[58] Field of Search .......... 128/203, 188, 139, 146, 128/146.3, 146.4, 146.5, 140 N, 142.3, 195, 198, 145.5, 176, 177

[56] References Cited
UNITED STATES PATENTS

| | | | |
|---|---|---|---|
| 1,632,449 | 6/1927 | McKesson | 128/195 |
| 3,625,206 | 12/1971 | Charnley | 128/139 |
| 3,696,832 | 10/1972 | Maurice et al. | 137/512.1 |
| 3,721,239 | 3/1973 | Myers | 128/188 |
| 3,738,360 | 6/1973 | Dryden | 128/188 |
| 3,752,186 | 8/1973 | Dryden | 128/188 |
| 3,814,091 | 6/1974 | Henkin | 128/145.5 |
| 3,877,691 | 4/1975 | Foster | 128/188 |

*Primary Examiner*—Robert W. Michell
*Assistant Examiner*—Henry J. Recla
*Attorney, Agent, or Firm*—Jack M. Wiseman

[57] ABSTRACT

A system for administering anaesthesia or analgesia to a patient in a safe and effective way while limiting the escape of the anaesthetic gases into the environment of the patient and the person administering the process.

12 Claims, 4 Drawing Figures

ANAESTHESIC SYSTEM

BACKGROUND OF THE INVENTION

In the administering of anaesthesic gases to patients a mask is placed over the nose or mouth of the patient and a controlled amount of the gas is permitted to flow into the mask. Inhalation of anaesthetic gas can be used to achieve a long range of predictable responses to pain which permits medical processes such as dental work to be performed on the patient with less sensation of pain.

In systems used previously a substantial amount of the gas either escaped or was emptied into the room in which the patient is located. Approximately 5 to 10 liters of gas are delivered to a patient under anaesthesia or analgesia.

Some of this gas is absorbed into the body of the patient but the excess gas is allowed to escape into the surrounding environment through a pressure relief valve. The gas which is absorbed into the body during anaesthesia also is exhaled by the patient as soon as the anaesthetic gas flow has been stopped resulting in virtually all the gas which has been administered to the patient under the present process being ultimately dumped into the room.

A growing concern for the side effects of the escaped gases on the health of the operating personnel has been voiced by many medical groups and committees. The high level of waste anaesthesia present in operatories today are unnecessary and possibly harmful to the personnel involved. Hospitals have already started to make moves to effectively scavenge the anaesthetic gases in their operatories to decrease the levels of gas inspired by their operating personnel. Dental offices on the other hand have had fewer regulations and levels that have been found in dental offices have been much higher and it is the aim of this product to help the dentist in his efforts to scavenge waste gases in the future. Thus it is the primary purpose of this invention to provide a process for administering anaesthesic gases in a manner to limit the exposure of the medical personnel to high concentrations of the gas both during the administering process and afterwards.

SUMMARY OF THE INVENTION

A method of administering anaesthesic gas to a patient by use of a mask which is placed over the patient's nose and/or mouth, which mask incorporates means to administer the anaesthesic gas and also includes means to retrieve expired anaesthesic gas and transport said expired gas and the uninhaled gas out of the environment of the administering personnel by the employment of a vacuum system.

DESCRIPTION OF THE INVENTION

Figure 2:
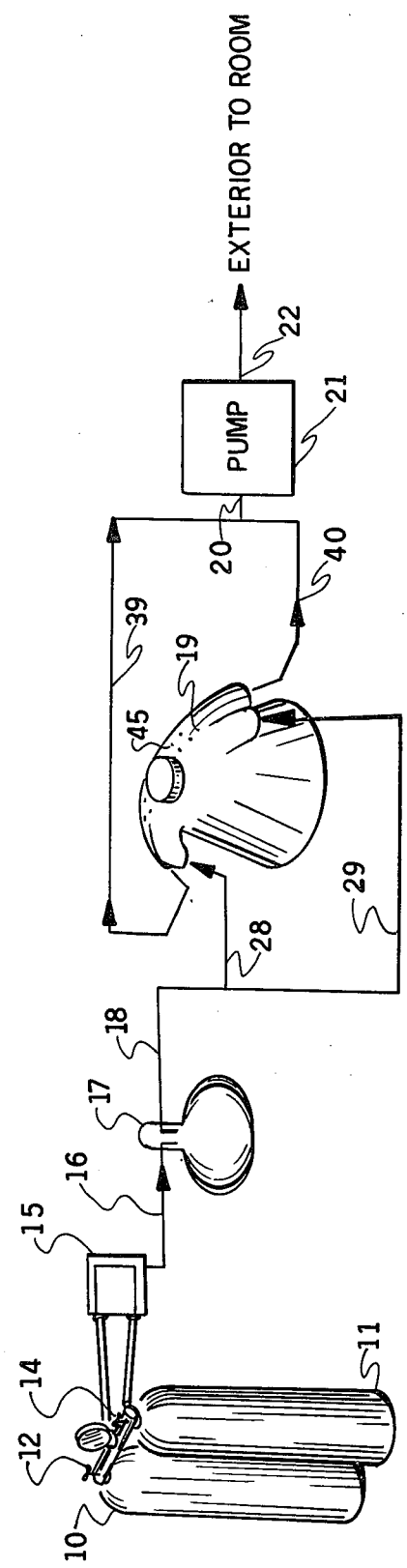
FIG. 2 is a schematic view of an anaesthesic gas-administering system incorporating the subject invention.

In FIG. 2 is shown a system for administering anaesthesic gas to a patient. As in prior systems, an anaesthesic gas such as oxygen and nitrous oxide is supplied from a pair of tanks 10 and 11 through shutoff valves 12 and 14, respectively, to a standard mixing valve 15. In the mixing valve the gases are mixed and fed into a supply line 16 through a gas bag 17 for passage through a line 18 to an anaesthesic gas mask 19. The overall gas flow rate is controlled at the mixing valve which is of a standard design having flow control means as well as means for joining the gases together. The person administering the flow can obtain a visual indication of the breathing volume and rate of the patient by observing the expansion and contraction of the bag 17. In addition, such person can also administer a rapid flow of the gas by grabbing and squeezing the bag which causes accelerated flow through the line 18 to the mask.

As discussed previously, the patient usually breathes only through the nose or mouth and it is over these organs that the mask is placed. In prior systems, the exhaled gas and the gas fed through the mask which is not inhaled is usually dumped directly into the room surrounding the patient which naturally raises the concentration of such gas in that room each time the anaesthesic process is performed. For instance in a dental office the process can be performed many times a day and if the air is not scavenged by passage through a non-recirculating air-conditioning system, the concentrations of the gas can become quite high. Such concentrations can reach the level at which the dentist's consciousness and dexterity are actually affected by the continuous breathing of the gas.

In accordance with the present invention, means are provided for receiving substantially all of the gases supplied to the patient and conducting such gases to a point exterior of the treatment room to maintain the concentration of the gases within the room at low levels. Thus there is provided a special anaesthesic mask 19 which is connected to an exhaust pump 21 such that gas exhaled by the patient, gas supplied to the mask but not inhaled by the patient and gas escaping around the mask are collected and pumped to a point exterior of the room by means of the pipe 20, the pump 21 and exhaust pipe 22 leading to a point exterior of the room.

Figure 1:
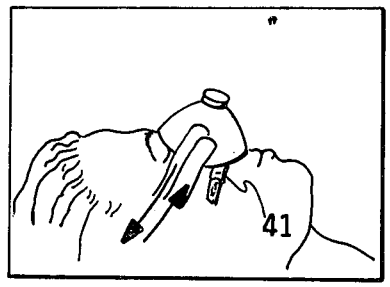
FIG. 1 shows the mask placed on a patient for administering an anaesthesic gas.
Figure 3:
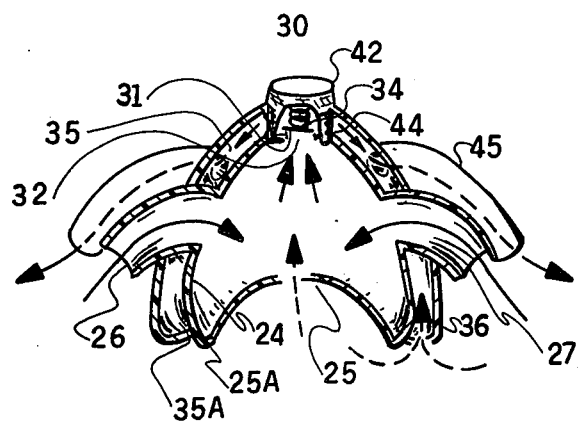
FIG. 3 is a cross-sectional view of an anaesthesic mask incorporating the present invention.
Figure 4:
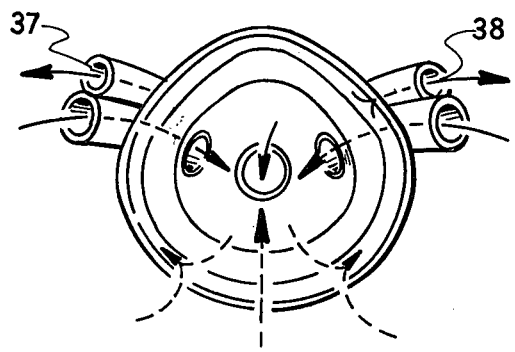
FIG. 4 is a bottom plan view of the anaesthesic mask of FIG. 3.

An anaesthesic mask for incorporation into the present invention is shown in FIGS. 3 and 4 comprises an inner mask made up of an inner shell 24 having an opening or chamber 25 therein which permits entry of the nose or exit of supplied gases into the mouth. Such inner mask has connected thereto a pair of inlet tubes 26 and 27 connecting through the lines 28 and 29 to the supply line 18 leading from the anaesthesic bag 17. Thus as gas glows through the supply line under the pressure of the gases supplied from the tanks 10 and 11, it is forced to flow into the gas cavity or chamber formed within the inner shell 24 from which it can be inhaled by the patient to which the gas is being administered. As pointed out before, the patient usually breathes through the nose and therefore the mask commonly is placed over the nose, however if the patient actually breathes through the mouth, either the mask can be placed only over the mouth or the mask can be made of sufficient size to fit over both the nose and the mouth.

In the present invention the mask is provided with a pressure relief valve 30 (FIGS. 2 and 3) which valve is normally closed by the plunger 31 being spring-loaded over an opening 32 in the inner shell. Thus the gas which enters the inlet lines is contained in the mask and can be readily inhaled by the patient. Upon exhalation by the patient, the pressure within this inner mask is immediately increased sufficiently to cause the plunger to compress the spring 34 to the position indicated in FIG. 4. Thus the exhaled gas is permitted to pass through the pressure relief valve and into an exhaust passage 35 formed between the inner shell 24 and an outer shell 36 surrounding but spaced from that inner shell. Communicating with the exhaust passage 35 are a pair of exhaust tubes 37 and 38 in flow relationship with the exhaust lines 39 and 40 which join at the juncture with the exhaust line 20 connecting with the exhaust pump 21.

In a normal mask not using an exhaust pump the exhalation by the patient will cause a substantial increase in the flow of gas into the inner mask such that gas will escape between the edges 25A of the mask and the patient's face. Naturally this leads to a substantial leakage of gas into the surroundings of the patient. However, by using an extract system providing a positive exhaust flow by use of the pump 21 creating a negative pressure within the exhaust lines 20, 39 and 40, the gas is scavenged from the mask to thereby limit leakage through the opening 25A and the patient's face.

In accordance with another feature of the invention, the inner exhaust passage 35 opens adjacent the face of the patient at a continuous port 35A surrounding the edge 25A of the inner mask. Thus by the creation of a negative pressure and because the peripheral edge of the outer shell extends past the peripheral edge 25A of the inner shell so as to press more tightly against the patient's face, any gas leaking between the juncture of the inner shell and the patient's face is immediately scavenged through the port 35A to the inner passage 35 and into the exhaust lines.

With the creation of a negative pressure between the inner and outer shells there exists the possibility that the mask will become pressed sufficiently close to the patient's face such that it will stick to the face because of the negative pressure within the passage 35 and the atmospheric pressure outside the mask. To counteract this possibility means may be provided to limit the negative pressure within the passage 35. One form of such means involves the location of a series of relief holes 45 in the outer shell 36 connecting the inner passage 35 with atmosphere. Such relief holes are not large enough to permit total relief of the vacuum pressure within the passage 35 but do permit sufficient air flow to limit such vacuum pressure. Of course an actual pressure relief valve can also be utilized if necessary which valve would control closely the vacuum pressure maintained within the inner passage 35.

The mask can also be provided with straps or strap attachments 41 for attachment of the mask to the head of the patient. In addition, the pressure relief valve can be made adjustable by the incorporation of a control knob 42 which is threaded into the outer wall 44. By tightening the thumb screw 42 the tension on the spring 34 can be increased to permit a higher buildup of pressure within the inner shell 24 prior to the opening of the valve. Such a higher buildup might be desirable to cause a quick flow of oxygen to the patient for medical purposes such as revival. Said valve also permits the administration of the gas to control the fullness of the gas cavity and the breathing reservoir.

In addition, another feature of the present invention involves the manufacture of the mask from material which is transparent. Such a transparent mask enables the administering personnel to visually observe the proper placement of the mask over the patient's nose and mouth. Also the transparent mask can be inspected easily to detect the presence of any foreign objects, dirt or other pocketing or buildup.

The invention claimed is:
1. A mask for administering gas to a patient comprising:
   a. an inner cup-shaped wall arranged to fit over the nose or mouth of a patient and to engage the face of the patient along the peripheral edge thereof to form a gas chamber between the face of the patient and the inner surface of said inner wall;
   b. an outer wall secured to and spaced from said inner wall to form an exhaust passage therebetween communicating with said chamber for receiving exhaust gas exhaled by the patient into said chamber and having a peripheral edge disposed in the vicinity of the peripheral edge of said inner wall defining means for receiving gas leaking between said peripheral edge of said inner wall and the face of the patient;
   c. means connected to said inner wall and communicating with said chamber for introducing gas into said chamber to be inhaled by the patient; and
   d. means connected to said outer wall and communicating with said exhaust passage for removing the exhaust gas and the leakage gas;
   e. pressure control means connected between said inner and outer walls for communicating said chamber with said exhaust passage, said pressure control means being arranged for gas to enter said chamber from said means for introducing gas into said chamber when the patient inhales gas and arranged for exhaled gas to enter said exhaust passage from said chamber when the patient exhales gas.

2. A mask as claimed in claim 1 wherein said inner wall is formed of a thin flexible material.

3. A mask as claimed in claim 2 wherein said outer wall has a cup shape and is formed of a thin flexible material.

4. A mask as claimed in claim 1 wherein said pressure control means comprises a pressure-relief valve interposed between said inner and outer walls in communication with said chamber and said exhaust passage, said pressure-relief valve being normally closed while gas enters said chamber from said means for introducing gas into said chamber to be inhaled by the patient, said pressure-relief valve being opened for exhaled gas to enter said exhaust passage from said chamber when the patient exhales gas.

5. A system for administering gas in a treatment room to a patient comprising:
   A. a mask comprising:
      a. an inner cup-shaped wall arranged to fit over the nose or mouth of a patient and to engage the face of the patient along the peripheral edge thereof to form a gas chamber between the face of the patient and the inner surface of said inner wall,
      b. an outer wall secured to and spaced from said inner wall to form an exhaust passage therebetween communicating with said chamber for receiving exhaust gas exhaled by the patient into said chamber and having a peripheral edge disposed in the vicinity of said peripheral edge of said inner wall defining means for receiving gas leaking between said peripheral edge of said inner wall and the face of the patient, c. means connected to said inner wall and communicating with said chamber for introducing gas into said chamber to be inhaled by the patient, and d. means connected to said outer wall and communicating with said exhaust passage for removing the exhaust gas and the leakage gas;

B. means connected to said means for introducing gas into said chamber for supplying gas to be inhaled by the patient; and C. means connected to said means for removing the exhaust gas and the leakage gas for conducting the exhaust gas and the leakage gas to an area removed from the patient's treatment room;

D. pressure control means connected between said inner and outer ealls for communicating said chamber with said exhaust passage, said pressure control means being arranged for gas to enter said chamber from said means for introducing gas into said chamber when the patient inhales gas, and arranged for exhaled gas to enter said exhaust passage from said chamber when the patient exhales gas.

6. A system as claimed in claim 5 wherein said means for conducting the exhaust gas and the leakage gas to an area removed from the patient's treatment room includes an exhaust pump.

7. A system as claimed in claim 6 wherein said inner wall is formed of a thin flexible material.

8. A system as claimed in claim 7 wherein said outer wall has a cup shape and is formed of a thin flexible material.

9. A system as claimed in claim 6 wherein said pressure control means comprises a pressure-relief valve interposed between said inner and outer walls in communication with said chamber and said exhaust passage, said pressure-relief valve being normally closed while gas enters said chamber from said means for introducing gas into said chamber to be inhaled by the patient, said pressure-relief valve being opened for exhaust gas to enter said exhaust passage from said chamber when the patient exhales gas.

10. A system as claimed in claim 9 wherein said pressure-relief valve includes adjusting means for regulating the force required to open under the pressure in said chamber for exhaust gas to enter said exhaust passage from said chamber.

11. A mask as claimed in claim 9 wherein said pressure-relief valve includes adjusting means for regulating the force required to open under the pressure in said chamber for exhaust gas to enter said exhaust passage from said chamber.

12. A system as claimed in claim 6 wherein said means including said exhaust pump creates a negative pressure to scavenge the gas leaking between the peripheral edge of said inner wall and the patient's face and comprising relief passages formed in said outer wall communicating with said exhaust passage and the atmosphere to reduce the tendency for the peripheral edge of said inner wall to adhere to the patient's face.

* * * * *

UNITED STATES PATENT OFFICE
CERTIFICATE OF CORRECTION

Patent No. 4,015,598            Dated April 5, 1977

Inventor(s) Glenn E. Brown

It is certified that error appears in the above-identified patent and that said Letters Patent are hereby corrected as shown below:

Column 4, line 26, the "and" should have been deleted;

Column 4, line 29, ---and--- should have been added after the semi-colon;

Column 5, line 12, the "and" should have been deleted;

Column 5, line 16, ---and--- should have been added after the semi-colon;

Column 5, line 18, "ealls" should have been ---walls---.

Signed and Sealed this

Twenty-fifth Day of October 1977

[SEAL]

Attest:

RUTH C. MASON          LUTRELLE F. PARKER
*Attesting Officer*     *Acting Commissioner of Patents and Trademarks*